United States Patent [19]

Abrahamson

[11] Patent Number: 5,319,979
[45] Date of Patent: Jun. 14, 1994

[54] LOAD CELL PRESSURE SENSOR FOR PUMP CASSETTE

[75] Inventor: Kent D. Abrahamson, Libertyville, Ill.

[73] Assignee: Abbott Laboratories, Abbott Park, Ill.

[21] Appl. No.: 991,024

[22] Filed: Dec. 15, 1992

[51] Int. Cl.$^5$ .............................................. G01L 9/00
[52] U.S. Cl. ............................................ 73/745; 73/723
[58] Field of Search .............. 128/DIG. 12, DIG. 13, 128/DIG. 3, 748, 675; 422/100, 112; 73/723, 745, DIG. 4

[56] References Cited

U.S. PATENT DOCUMENTS

| | | | |
|---|---|---|---|
| 3,738,356 | 6/1973 | Workman | 128/675 |
| 4,674,335 | 6/1987 | Wendt | 73/745 |

Primary Examiner—Richard E. Chilcot, Jr.
Assistant Examiner—Joseph L. Felber
Attorney, Agent, or Firm—A. Nicholas Trausch

[57] ABSTRACT

The present invention relates to a compression load cell used to monitor pressure in a diapragm cassette pumping system. A plunger is axially slidable in a linear bearing and has a first end in contact with the cassette and the second end in contact with the load cell. The force signals have a direct relationship with the pressure in the cassette.

4 Claims, 4 Drawing Sheets

LOAD CELL PRESSURE SENSOR FOR PUMP CASSETTE

FIELD OF THE INVENTION

The present invention relates generally to a diaphragm pump system which can be used for preparation of parenteral solutions or intravenous infusion, and more particularly to a pressure monitoring device for externally monitoring the pressure within a disposable pumping cassette used with the pumping apparatus.

BACKGROUND OF THE INVENTION

In the health care field, it is becoming increasingly common to use disposable pumping cassettes for pumping medical solutions. The cassettes are made of plastic and are operated by non-disposable driver mechanisms external to the cassette. Disposable cassette pumps offer many advantages over pumps with permanent pumping chambers. For example, disposable cassette pumps can be easily set up and readily changed over from prior pumping procedures without the need for sterilizing the permanent pump apparatus. Further, the disposable cassette pump apparatus allows for regular changing of the pumping pathway to reduce the risk of contamination without taking the pump equipment out of use for the period of time needed to sterilize the equipment.

Monitoring the pressure of the fluid being pumped through the cassette can provide useful information for controlling the pump. As disclosed in U.S. Pat. No. 4,457,753 monitoring cassette pressure permits the detection of occlusions or plugged filters in the cassette outlet line leading to a patient, for example. As disclosed in U.S. Pat. No. 4,842,584 monitoring cassette pressure also permits the valves to be checked for leakage. Further, when used as an infusion system, monitoring the discharge pressure of the cassette can be used to determine the patient's blood pressure.

U.S. Pat. No. 4,950,244 to Fellingham et al, hereby incorporated by reference, discloses a pressure transducer which can detect occlusions in the cassette inlet line from the solution container to the cassette.

However, while the above described pressure monitors are accurate, they are very complex and various parameters associated with the cassette must be strictly controlled. The need to control the parameters reduces the flexibility that the pumping apparatus can be used in and creates the potential for inaccurate results if the pump is used outside the controlled range of parameters. Thus there is a need for a simplified pressure sensor than can make accurate pressure measurements without the need for strict control of certain parameters.

SUMMARY OF THE INVENTION

The present invention is a pressure detection mechanism for a processor control pumping apparatus using a diaphragm pumping cassette which includes a sensor housing mechanism mounted in the pumping apparatus. A force sensing mechanism is mounted in the housing. A sensor pin or plunger is axially slidable in the housing and has a first end adapted for perpendicularly abutting the diaphragm of the cassette and a second plunger end adapted for abutting contact with the force sensing mechanism. A biasing spring is mounted on the housing for biasing the sensing mechanism into the housing. A linear bearing supports the sensor pin for axial sliding movement. Means for transmitting force signals from the sensing mechanism to the processor of the pump apparatus are also provided. Other features of the invention will be discussed in details below.

The pressure sensor assembly of the present invention can detect pressures in the cassette, both above and below atmospheric pressure (i.e. 0 psig). These pressure measurements allow for the determination of distal and proximal occlusions, cycle times, and leak checks.

DETAILED DESCRIPTION OF THE PREFERRED EMBODIMENT

Figure 1:
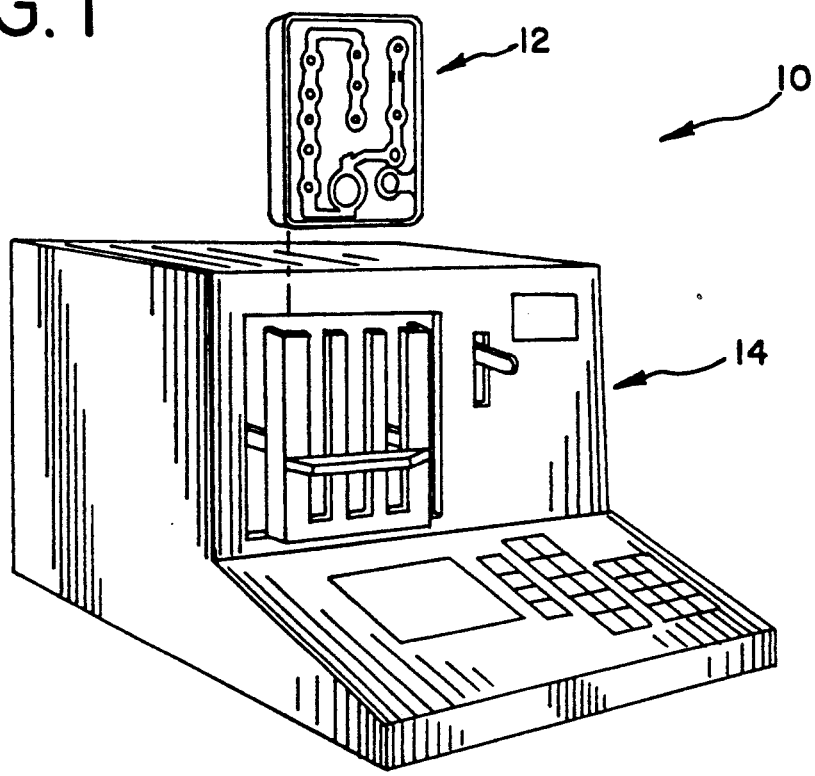
FIG. 1 is a perspective view of a solution pumping system, including a pump driver and a disposable pump cassette, which is operable in accordance with the principles of the present invention.

While the present invention is capable of embodiments in various forms, there is shown in the drawings and there will hereinafter be described a presently preferred embodiment, with the understanding that the present disclosure is to be considered as an example of the invention, and is not intended to limited the invention to the specific embodiment illustrated.

For the purpose of disclosing the present pressure monitoring invention, the operation of an exemplary diaphragm pumping apparatus will be described in detail. As will be appreciated, the controls of the pumping apparatus are preferably programmed to perform the sequence of steps of the present invention in an automated fashion. Efficient, predictable, and reliable operation of the pumping system is achieved in this manner.

With reference now to FIG. 1 of the drawings, therein is illustrated a solution pumping system 10. The illustrated system is a solution compounder, similar in operation to the Nutrimix ® Micro Compounder manufactured by Abbott Laboratories. The compounder is suitable for compounding and preparing parenteral solutions for subsequent administration to patients. However, it will be appreciated that a diaphragm pumping system operable in accordance with the disclosed invention can be readily configured for infusion of solutions or other medical applications.

The solution pumping system includes a disposable pump cassette 12 which is removably positionable in operative association with a pump driver 14. The cassette is fluidly connected by an appropriate fluid tubing transfer set (not shown) with solution containers (not shown) to be compounded and with a receiving bag (not shown) into which appropriate quantities of the various solutions are mixed. The resultant admixture is thus ready for patient administration. This compounding system would ordinarily be used in the pharmacy of a health care facility.

Alternatively, the diaphragm pumping apparatus could be in the form of an infusion pump such as the LifeCare ® 5000 Drug Delivery System which is also manufactured by Abbott Laboratories.

Figure 2:
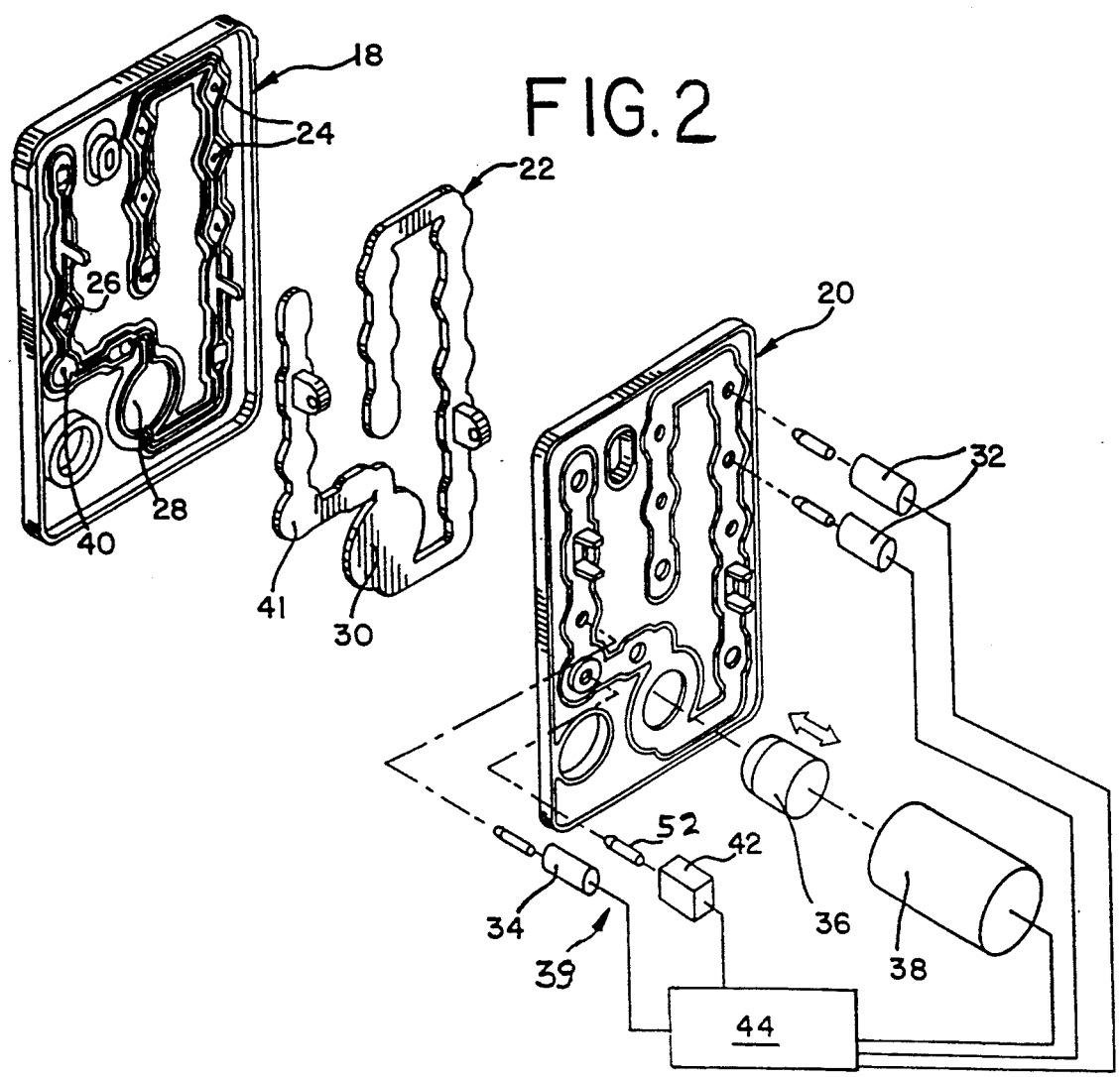
FIG. 2 is a diagrammatic, exploded perspective view illustrating the construction of the pump cassette shown in FIG. 1, and the manner in which the components of the associated pump driver cooperate with the pump cassette.

U.S. Pat. No. 5,062,774 to Kramer et al., hereby incorporated by reference discloses in greater details features of the illustrated compounding pumping system. Disposable pump cassette 12 of the system includes a cassette body comprising juxtaposed front 18 and rear 20 body members and a membrane-like elastomeric diaphragm 22 positioned in sandwich-like relationship between the front and rear cassette members, as shown for example in FIG. 2.

The front and rear cassette members are joined to each other such as by ultrasonic welding so that the rear cassette member 20 holds the elastomeric diaphragm 22 in tight conforming relationship with the front cassette member 18. In this way, the diaphragm and the front cassette member together define a liquid flow path through which solutions flows within the cassette.

The cassette preferably includes a plurality of liquid inlets which are configured to be joined through suitable tubing conduits to solution containers. The cassette further includes at least one liquid outlet which is connected by a suitable tubing component to the receiving container for the solution admixture.

Liquid is pumped through the cassette by a self-contained positive displacement pump of the pumping assembly. In particular, the front cassette member includes a bowl-like pumping chamber 28 with the diaphragm including a pump portion 30 positioned adjacent to the pump chamber.

Liquid flow through the cassette is controlled by a plurality of valves such as for example solenoid operated valve actuators 32 of the pump driver. The valve actuators are operable through openings defined in the rear 20 of the cassette member, with the actuators acting against respective portions of the diaphragm to cooperate in valve like manner with the valve seats defined by the front cassette member. Thus, each of the various liquid inlets is controlled by respective valve actuator, with the liquid outlet similarly controlled by respective valve actuator 34.

The positive displacement pump of the cassette is operated by a reciprocal pump piston or plunger 36 of the pump driver in accordance with U.S. Pat. Nos. 4,639,245; 4,818,186; 4,842,584; and 4,927,411 to Pastrone et al., all of which are hereby incorporated by reference herein. Essentially, liquid flow is effected by reciprocation of the pump piston in time relation to operation of inlet and outlet actuators. A reversible stepping motor 38 provides reciprocal stroking of the pump piston for alternately deforming and relaxing the pump portion of the diaphragm. This motion effects positive displacing of the liquid of the pump chamber 28. During the advancing stroke of the pump piston, the diaphragm portion is displaced into the pump chamber, with the outlet being opened by appropriate action of its actuator. Liquid displacement on the order of 0.75 ml is typical in a current embodiment. During the return stroke of the pump piston, the outlet is closed and an appropriate one of the inlets is opened by operation of its respective actuator. During the return stroke, the resilient pump portion of the diaphragm creates a negative pressure within the pump chamber, thus refilling the chamber with liquid for completing the pump cycle.

In order to monitor liquid pressures created within the pump cassette by the positive displacement pump, the present system preferably includes a force sensor assembly 39 incorporated into the pump driver. The front cassette member 18 defines a pressure chamber 40 in connection with the diaphragm. The portion 41 of the diaphragm adjacent the pressure chamber is engaged by the probe-like portion 52 of the pressure sensor. The force sensor 42 is operatively connected with the automated, programmable controls 44 of the present pump apparatus. The controls are preferably integrated into the pump driver, with the controls operatively connected with the various valve actuators, stepper motor, and other sensors of the system for effecting integrated operation thereof, including monitoring and analyzing occlusions in the system, cycle performance, and leak tests.

Figure 3:
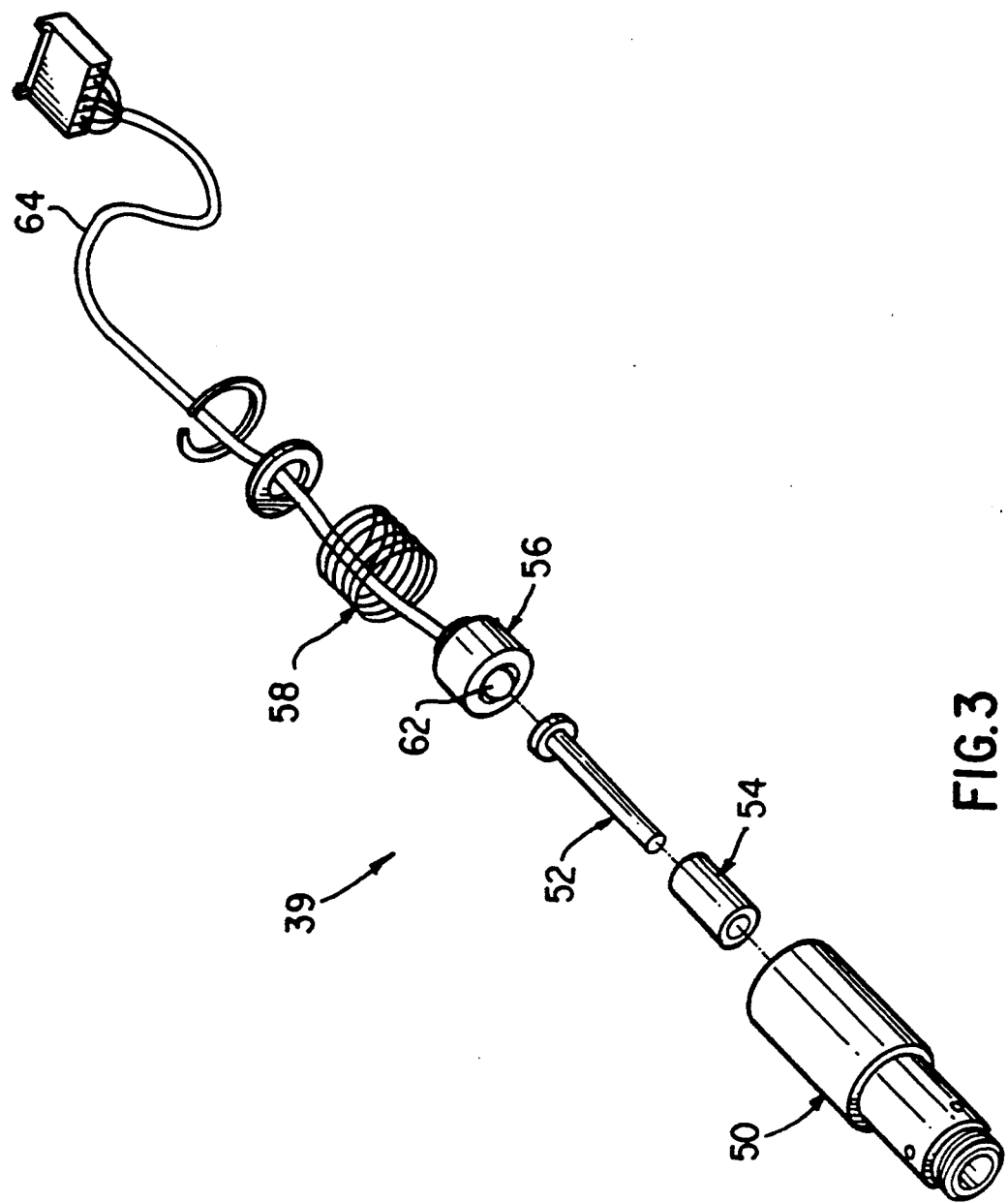
FIG. 3 is an exploded perspective view illustrating the construction of the pressure monitoring assembly of the present invention.
Figure 4:
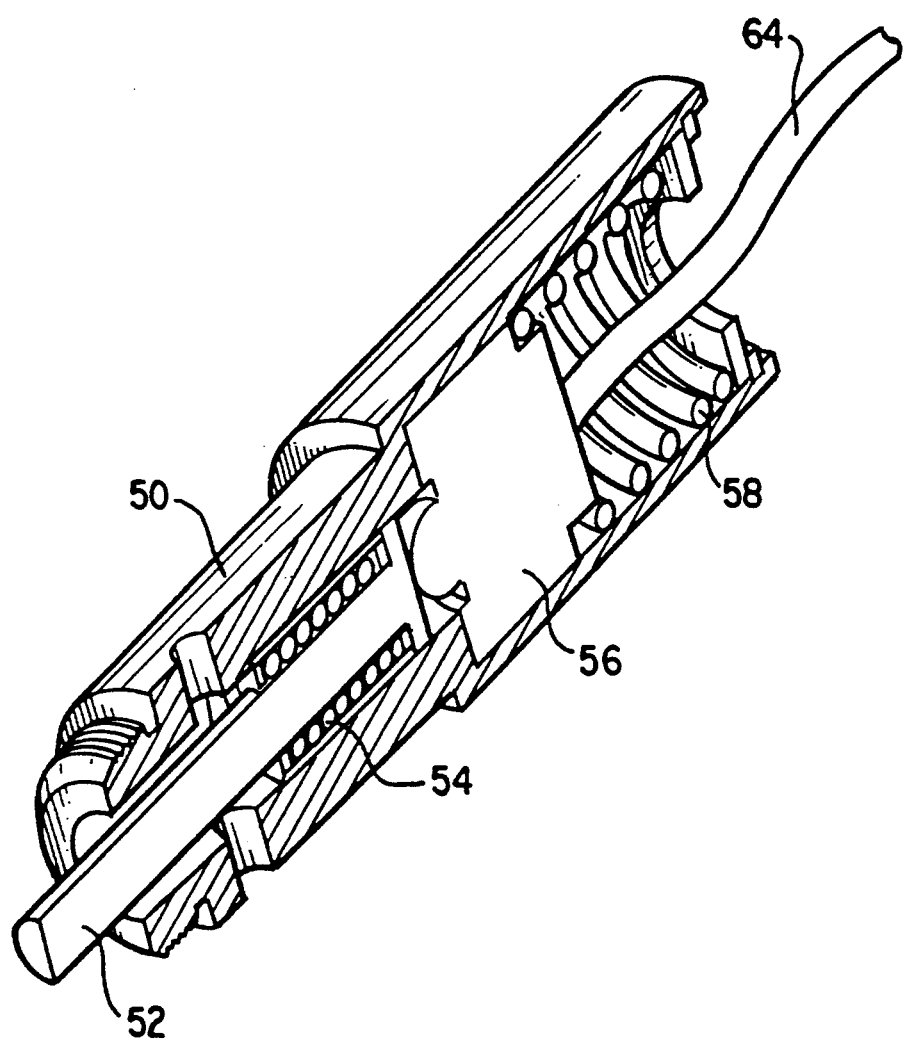
FIG. 4 is a cross sectional view illustrating an assembled pressure monitoring system according to the present invention.

As best seen in FIGS. 3 and 4, the pressure monitor includes a tubular housing member 50. Positioned inside of the housing is a pin or plunger member 52 that is axially slidable in linear bearing member 54. A compression load cell 56 is in contact with a second end of the plunger 52. A coil spring holds the load cell 56 in bias position against the housing 50. Thus the force sensing member 62 of the load cell can detect any movement of the plunger 52.

The electronic signal from this force is transmitted by cable 64 to the processor element 44 of the pump apparatus.

The pressure monitoring system of the present invention is thus primarily a linear system that includes the pressure sensor pin or plunger 52, the linear bearing 54, the compression spring 58, and a rigid load cell 56. The fundamental principle of the invention is to make the difference in stiffness between the cassette diaphragm and the load cell very large. Thus the stiffness of the system is dominated by the load cell. Any variation of the diaphragm's stiffness, which is inherently very large due to the properties of the diaphragm material, does not affect the force output signal of the system. For example, the stiffness of the system is equal to the stiffness of the diaphragm plus the stiffness of the load cell. Thus, if the stiffness of the diaphragm has a variation of ±20 percent, and if it is required that the error caused by this variation be less than 0.2 percent, then the stiffness of the load cell divided by the stiffness of the diaphragm will be in the range of a magnitude of 100.

In previous pressure sensors, as for example in the previously referenced U.S. Pat. No. 4,950,244 to Fellingham et al., the thin beam load cell creates a very complex pressure monitoring system wherein the stiffness of the thin beam is close to the stiffness of the diaphragm. Diaphragm stiffnesses have a large range of variability and can thus effect pressure readings. Eliminating the variable influence of the diaphragm stiffness improves the accuracy of the pressure sensor system by making it independent of the diaphragm stiffness. This allows more accuracy in pressure measurements and more flexibility in the parameters to be controlled, such as for example the diaphragm material.

In addition, the sensing system of the present invention has improved protection from axial and radial overloads. Damage due to axial overloads are prevented by using the spring 58 which can both hold the load cell 56 in position during operation and also deflect during an axial overload condition. Damage due to radial overloads are prevented by using a linear bearing 54 to both guide the pressure sensing pin 52 during operation and support radial overloads. The pressure sensor pin 52 has a flat surface which makes contacts with the spherical end of the load cell. This protects the load cell because only the axial loads are transmitted to the strain element of the load cell.

From the foregoing, it will be observed that numerous modifications and variations can be effected without departing from the true spirit and scope of the novel concept of the present invention. It is to be understood that no limitation with respect to the specific embodiment is intended or should be inferred. This disclosure is intended to cover, all modifications as fall within the scope of the appended claims.

What is claimed is:

1. A pressure detection mechanism for use with a processor controlled pumping apparatus having a removable pumping cassette, the detection mechanism comprising:

a mechanism housing mounted in the pumping apparatus;

means for sensing force mounted in the housing;

a plunger axially slidable in the housing having a first and second end, the first plunger end adapted for perpendicular abutting contact with the pumping cassette, the second plunger end adapted for abutting contact with the force sensing means;

bearing means mounted in the housing for providing axial sliding for the plunger to axially contact the sensing means;

biasing means mounted on the housing for biasing the sensing means axially into contact with the housing; and means for transmitting force signals from the sensing means to the processor of the pumping apparatus.

2. The pressure sensor of claim 1 wherein the sensing means is a compression load cell.

3. The pressure sensor of claim 2 wherein the bearing means is a linear bearing.

4. The pressure sensor of claim 3 wherein the biasing means is a helical spring.

* * * * *